(12) United States Patent
Yin

(10) Patent No.: US 10,005,093 B2
(45) Date of Patent: Jun. 26, 2018

(54) FOREIGN OBJECT DETECTING DEVICE AND COATING SYSTEM

(71) Applicants: BOE TECHNOLOGY GROUP CO., LTD., Beijing (CN); HEFEI BOE OPTOELECTRONICS TECHNOLOGY CO., LTD., Hefei, Anhui (CN)

(72) Inventor: Dongdong Yin, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 5 days.

(21) Appl. No.: 15/094,023

(22) Filed: Apr. 8, 2016

(65) Prior Publication Data

US 2016/0332182 A1     Nov. 17, 2016

(30) Foreign Application Priority Data

May 11, 2015  (CN) .......................... 2015 1 0237955

(51) Int. Cl.
*B05B 12/00*     (2018.01)
*G01D 5/34*      (2006.01)
(Continued)

(52) U.S. Cl.
CPC ............ *B05B 12/12* (2013.01); *G01D 5/342* (2013.01); *H01L 21/6715* (2013.01); *H01L 21/67288* (2013.01); *G01N 2021/9513* (2013.01)

(58) Field of Classification Search
None
See application file for complete search history.

(56) References Cited

U.S. PATENT DOCUMENTS

| 2010/0091063 A1 | 4/2010 | Nagata | |
| 2010/0310757 A1* | 12/2010 | Ooshiro | ................ B05C 5/0291 427/8 |
| 2013/0236990 A1* | 9/2013 | Sato | ........................ H01L 22/20 438/5 |

FOREIGN PATENT DOCUMENTS

| CN | 201281691 Y | 7/2009 |
| CN | 101933650 A | 1/2011 |

(Continued)

OTHER PUBLICATIONS

Office Action dated Oct. 9, 2016 issued in corresponding Chinese Application No. 201510237955.3.

(Continued)

*Primary Examiner* — Jethro M Pence
(74) *Attorney, Agent, or Firm* — Nath, Goldberg & Meyer; Joshua B. Goldberg

(57) ABSTRACT

The present disclosure provides a foreign object detecting device and a coating system. The foreign object detecting device includes a light emitting unit and a light receiving unit arranged side by side, the light emitting unit is used for emitting light towards a surface of a substrate to be detected, and the light receiving unit is used for detecting an optical signal of reflected light reflected from the surface of the substrate to be detected and capable of outputting the detected optical signal, and the optical signal includes brightness distribution information of the reflected light and position information of reflective spot. In the present disclosure, the foreign object is detected by emitting light towards the substrate and detecting change in brightness of the reflected light.

16 Claims, 4 Drawing Sheets

(51) Int. Cl.
  *B05B 12/12* (2006.01)
  *H01L 21/67* (2006.01)
  *G01N 21/95* (2006.01)

(56) References Cited

FOREIGN PATENT DOCUMENTS

| CN | 102192915 | A |   | 9/2011  |           |
|----|-----------|---|---|---------|-----------|
| CN | 103353459 | A |   | 10/2013 |           |
| CN | 203259481 | U | * | 10/2013 | G01N 21/958 |
| CN | 203396719 | U | * | 1/2014  | C01N 21/958 |
| CN | 203502360 | U |   | 3/2014  |           |
| CN | 103698910 | A |   | 4/2014  |           |
| JP | 2007-85960 | A |  | 4/2007  |           |

OTHER PUBLICATIONS

Second Office Action dated Apr. 1, 2017 in corresponding Chinese Patent Application No. 201510237955.3.

\* cited by examiner

FOREIGN OBJECT DETECTING DEVICE AND COATING SYSTEM

FIELD OF THE INVENTION

The present disclosure relates to the technical field of manufacturing display panels, and particularly to a foreign object detecting device and a coating system including the foreign object detecting device.

BACKGROUND OF THE INVENTION

Coating equipment is one of the crucial process equipment in the display manufacturing industry. A nozzle is the most important and precise component of the coating equipment, and is used for coating a photoresist liquid on the surface of a substrate to form a uniform photoresist film. During the coating process, a foreign object (such as glass chips, a coagulum of dropped photoresist liquid, or the like) often exists on the surface of a platform of the coating equipment or the substrate, and the foreign object may collide with the nozzle and damage the tip of the nozzle when the height of the foreign object exceeds a coating height.

An existing foreign detecting device generally detects the foreign object by using a laser sensor to perform point-line scanning. FIG. 1 is a top view of an existing foreign object detecting device (the hollow arrow in the figure indicates the coating direction). As shown in FIG. 1, a substrate 101 is placed on a platform 102, a nozzle 103 is disposed above the substrate 101, and a laser sensor, which includes a laser transmitter 104 and a laser receiver 105, is provided in front of the nozzle 103 in the coating direction. When a foreign object 106 is present on the substrate 101, as shown in FIGS. 2a and 2b (the hollow arrow in the figure indicates the laser direction), the laser emitted from the laser transmitter 104 is blocked by the foreign object, then the laser receiver 105 receives the laser with weakened intensity, and thus the presence of the foreign object 106 is detected.

However, the above detecting method has the following shortcomings: first, in the case of a foreign object 106 under the substrate 101, as shown in FIGS. 3a and 3b (the hollow arrow in the figure indicates the laser direction), since it is the elevated substrate 101 that is directly scanned, the laser can still arrive at the laser receiver 105, and as a result, the detection sensitivity is unsatisfactory, the foreign object 106 cannot be detected effectively, and the elevated substrate 101 collides with the nozzle 103 to cause greater damage; in addition, the point-line scanning can determine the position of the foreign object 106 in the coating direction (i.e., X direction as shown in FIG. 1) only, but cannot determine the position of the foreign object 106 in the Y direction as shown in FIG. 1, so it is difficult to quickly obtain the specific position of the foreign object 106.

SUMMARY OF THE INVENTION

An object of the present disclosure is to provide a foreign object detecting device and a coating system including the same, to achieve plan detection of a foreign object on or under the substrate.

In order to realize the above object, as a first aspect of the present disclosure, there is provided a foreign object detecting device, comprising a light emitting unit and a light receiving unit arranged side by side, wherein, the light emitting unit is used for emitting light towards a surface of a substrate to be detected, and the light receiving unit is used for detecting an optical signal of reflected light reflected from the surface of the substrate to be detected and capable of outputting the detected optical signal, and the optical signal includes brightness distribution information of the reflected light and position information of a reflective spot.

Preferably, both the light emitting unit and the light receiving unit are strip-like, and lengths of both the light emitting unit and the light receiving unit are greater than or equal to width of the substrate to be detected.

Preferably, the light emitting unit is capable of emitting light perpendicular to the substrate to be detected.

Preferably, the light emitting unit comprises a light transmissive box, and a strip-like light source and a focusing lens disposed in the light transmissive box, a slit is arranged at one side of the light transmissive box facing the substrate to be detected, extending direction of the slit is the same as that of the strip-like light source, and light emitted from the strip-like light source exits via the slit after converged by the focusing lens.

Preferably, the light emitting unit further comprises a light guide plate disposed between the strip-like light source and the focusing lens.

Preferably, the strip-like light source comprises a strip-like light emitting diode, a plurality of light emitting diodes arranged in a strip-like dot matrix, or a strip-like laser transmitter.

Preferably, the light receiving unit comprises a plurality of CCD cameras arranged in a strip or a strip-like photodetector.

As a second aspect of the present disclosure, there is provided a coating system, comprising a nozzle and the above foreign object detecting device provided by the present disclosure, and the foreign object detecting device is fixed in front of the nozzle in a coating direction.

Preferably, the coating system further comprises a control unit, which is connected to the light receiving unit of the foreign object detecting device to receive the optical signal from the light receiving unit, and is also connected to the nozzle to transmit a control signal to the nozzle, the control unit is capable of processing the received optical signal and making a judgement, and if the control unit judges that brightness value of reflected light from a certain reflective spot is smaller than a preset value according to the optical signal, the coating system is controlled to stop operation.

Preferably, the coating system further comprises a driving device, an output terminal of the driving device is connected to the nozzle to drive the nozzle to move above the substrate, and a control terminal of the driving device is connected to the control unit to receive a control signal from the control unit; if the control unit judges that the brightness value of reflected light from a certain reflective spot is smaller than the preset value according to the optical signal, the control unit transmits the control signal to the control terminal of the driving device, to control the driving device to stop outputting power to the nozzle.

Preferably, the control unit comprises a signal converting module and a judging module, the signal converting module is used for converting the optical signal into an electrical signal which includes information on dimension of the foreign object and position of the foreign object, and the judging module is used for comparing the dimension of the foreign object indicated by the electrical signal with a preset threshold dimension, to judge whether the dimension of the detected foreign object exceeds a preset range or not.

Preferably, the control unit further comprises a model establishing module and a display module, the model establishing module is connected to the signal converting module, and is used for establishing a three-dimensional model, which presents state of the foreign object on the substrate, according to the electrical signal obtained by the signal converting module, and the display module is used for demonstrating the three-dimensional model.

Preferably, the state of the foreign object on the substrate includes the position of the foreign object on the substrate and the dimension of the foreign object.

Preferably, the dimension of the foreign object includes an area occupied by the foreign object and a height of the foreign object.

Preferably, the control unit further comprises an alarming module connected to the judging module; if the judging module judges that the dimension of the foreign object exceeds the threshold dimension according to the electrical signal, the judging module sends an abnormality signal to the alarm module, and the alarm module sends out an alarming signal upon receipt of the abnormality signal.

In the present disclosure, the light emitting unit and the light receiving unit are provided side by side above the substrate, the foreign object is detected by emitting light towards the surface of the substrate and detecting change in brightness of the reflected light. As compared with the prior art, not only the foreign object on the substrate but also the foreign object under the substrate can be detected effectively, and the substrate elevated by the foreign object thereunder is prevented from colliding with the nozzle in the present disclosure.

In addition, in the present disclosure, the foreign object can be detected in plan manner, a 3D model can be established according to the detected data so as to stereoscopically display the dimension of the foreign object and the position of the foreign object on the substrate, and thus the present disclosure can determine the specific position of the foreign object more quickly as compared with the prior art in which only the position of the foreign object in a single direction can be detected.

BRIEF DESCRIPTION OF THE DRAWINGS

The accompanying drawings, which constitute a part of the specification, are used for providing a further understanding of the present disclosure, and explaining the present disclosure in conjunction with the following specific implementations, but not intended to limit the present disclosure. In the accompanying drawings.

DETAILED DESCRIPTION OF THE EMBODIMENTS

Specific implementations of the present disclosure will be described in detail below in conjunction with the accompanying drawings. It should be understood that, the specific implementations described herein are merely used for describing and explaining the present disclosure, rather than limiting the present disclosure.

Figure 1:
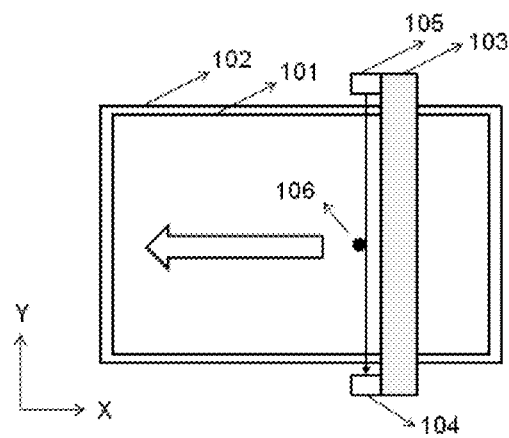
FIG. 1 is a top view of a foreign object detecting device in the prior art.
Figure 2A:
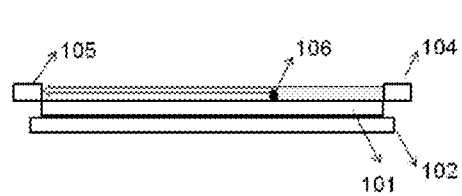
FIGS. 2a and 2b are side views, respectively along X direction and Y direction as shown in FIG. 1, of the foreign object detecting device in FIG. 1 in the case where a foreign object exists on a substrate.
Figure 2B:
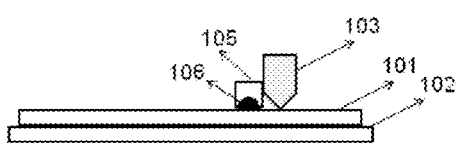
Figure 3A:
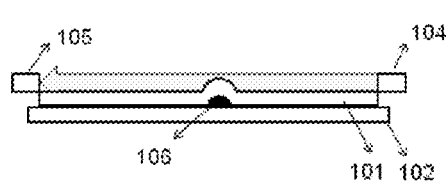
FIGS. 3a and 3b are side views, respectively along X direction and Y direction as shown in FIG. 1, of the foreign object detecting device in FIG. 1 in the case where a foreign object exists under the substrate.
Figure 3B:
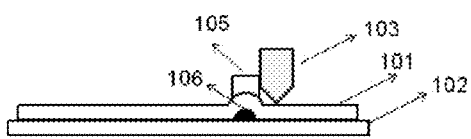
Figure 4:
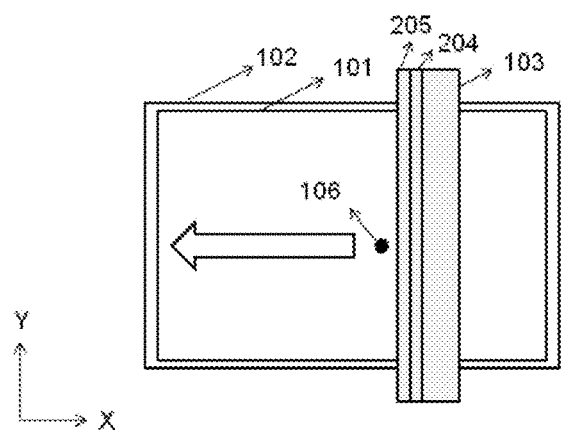
FIG. 4 is a top view of a foreign object detecting device in an embodiment of the present disclosure.
Figure 5:
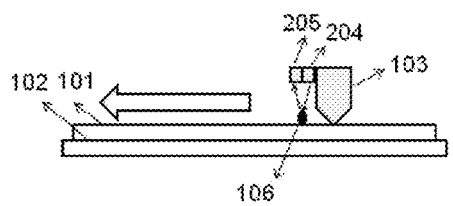
FIG. 5 is a side view of a foreign object detecting device in the embodiment of the present disclosure.

An embodiment of the present disclosure provides a foreign object detecting device, FIGS. 4 and 5 are a top view and a side view of the foreign object detecting device according to the embodiment of the present disclosure, respectively, and the hollow arrows in the figures indicate the coating direction.

The foreign object detecting device includes a light emitting unit 204 and a light receiving unit 205 arranged side by side, the light emitting unit 204 is used for emitting light towards a surface of a substrate 101 to be detected, the substrate 101 being placed on a platform 102, and the light receiving unit 205 is used for detecting an optical signal of reflected light reflected from the surface of the substrate 101 and capable of outputting the detected optical signal, and the optical signal includes brightness distribution information of the reflected light and position information of a reflective spot.

Figure 6A:
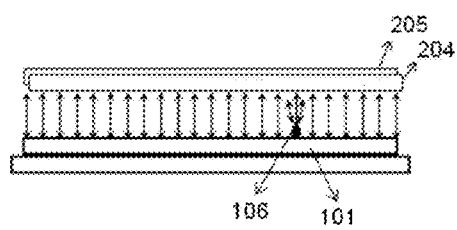
FIGS. 6a and 6b are schematic diagrams illustrating the principles of detecting a foreign object on a substrate and detecting a foreign object under a substrate in the foreign object detecting device according to the embodiment of the present disclosure, respectively.
Figure 6B:
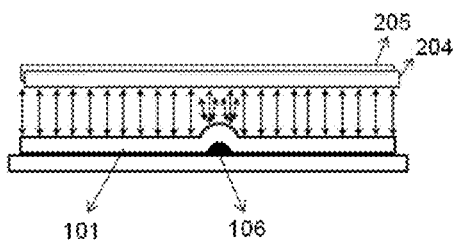

FIGS. 6a and 6b are schematic diagrams illustrating the principles of detecting a foreign object on the substrate and detecting a foreign object under the substrate in the foreign object detecting device according to the embodiment of the present disclosure, respectively. Specifically, FIG. 6a illustrates the case where the foreign object 106 exists on the substrate 101, and FIG. 6b illustrates the case where the foreign object 106 exists under the substrate 101. When the foreign object 106 exists on the substrate 101, as shown in FIG. 6a, the light irradiating on the foreign object 106 is subject to diffuse reflection, reflected light from the reflective spot corresponding to the position of the foreign object 106 has a reduced brightness, that is, the brightness of the reflected light from the position corresponding to the foreign object 106 is lower than that of reflected light from other position on the substrate 101, and therefore, based on the detected position where the reflected light has a reduced brightness, the position of the foreign object 106 can be determined.

Similarly, when the foreign object 106 exists under the substrate 101, as shown in FIG. 6b, the part of the substrate 101 corresponding to the position of the foreign object 106 is elevated, the light irradiating on the elevated part is subject to diffuse reflection, and reflected light from the reflective spot corresponding to the position of the foreign object 106 has a reduced brightness, so based on the detected positon where the reflected light has a reduced brightness, the position of the foreign object 106 can be determined.

Moreover, if the area occupied by the foreign object 106 or the height of the foreign object 106 varies, the reflected light has different brightness. In general, the greater area occupied by the foreign object 106 or the larger height of the foreign object 106, the lower brightness of the reflected light. Therefore, the specific dimension of the foreign object can be calculated based on specific distribution of brightness of the reflected light. For example, the area occupied by the foreign object can be calculated based on the area of the region where the received reflected light has a reduced brightness, the height of the foreign object can be calculated based on the extent by which the brightness of the received reflected light is reduced, and so on.

In the present disclosure, the foreign object is detected by emitting light towards the substrate 101 and detecting change in brightness of the reflected light. As compared with the prior art, not only the foreign object 106 on the substrate 101 but also the foreign object 106 under the substrate 101 can be detected effectively, and the substrate 101 elevated by the foreign object 106 thereunder is prevented from colliding with the nozzle in the present disclosure.

In addition, in the present disclosure, the foreign object 106 can be detected in plan manner, and thus the present disclosure can determine the specific position of the foreign object 106 more quickly as compared with the prior art in which only the position of the foreign object 106 in a single direction (coating direction) can be detected.

Further, as shown in FIG. 4, both the light emitting unit 204 and the light receiving unit 205 are strip-like, and lengths of both the light emitting unit 204 and the light receiving unit 205 are greater than or equal to the width of the substrate to be detected. When the foreign detecting device moves along the coating direction, the entire surface of the substrate 101 can be scanned, thereby improving the efficiency of the foreign object detection.

Preferably, the light emitting unit 204 can emit light perpendicular to the substrate 101. As shown in FIGS. 6a and 6b, when incident light irradiates on the substrate vertically, diffuse reflection at the position of the foreign object 106 is the most significant, and the change in brightness at the position of the foreign object 106 can be detected more easily by the light receiving unit 205 as compared with the position without the foreign object.

Figures 7A, 7B:
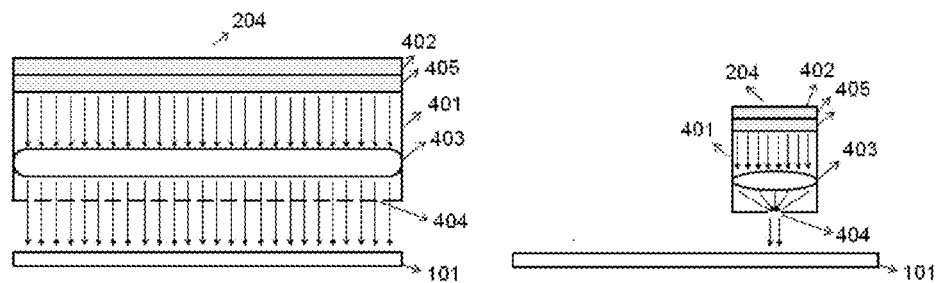
FIGS. 7a and 7b are side views, respectively along X direction and Y direction in FIG. 4, of a light emitting unit in the foreign object detecting device according to the embodiment of the present disclosure.

The specific forms of the light emitting unit 204 and the light receiving unit 205 are not limited in the present application, and in order to improve collimation of detecting light, the light emitting unit 204 shown in FIGS. 7a and 7b may be adopted. FIGS. 7a and 7b are side views, respectively along X direction and Y direction as shown in FIG. 4, of a light emitting unit in the foreign object detecting device according to the embodiment of the present disclosure.

As shown in FIGS. 7a and 7b, the light emitting unit 204 includes a light transmissive box 401, and a strip-like light source 402 and a focusing lens 403 disposed in the light transmissive box 401, a slit 404 is arranged at one side of the light transmissive box 401 facing the substrate 101, the extending direction of the slit 404 is the same as that of the strip-like light source 402, and the light emitted from the strip-like light source 402 exits via the slit 404 after converged by the focusing lens 403. In general, in order to enhance uniformity of light, the light emitting unit 204 further includes a light guide plate 405 disposed between the strip-like light source 402 and the focusing lens 403.

In the embodiment, the light guide plate 405 is used to diffuse light emitted from the strip-like light source 402, so as to obtain parallel detecting light with uniform brightness, then the detecting light is converged by the focusing lens 403, so as to obtain strip-like detecting light with high brightness, and the strip-like detecting light finally exits via the slit 404, thus ensuring collimation and uniformity of the resultant detecting light.

The strip-like light source 402 in the embodiment may include any one of a strip-like light emitting diode, a plurality of light emitting diodes arranged in a strip-like dot matrix, and a strip-like laser transmitter. In the above light source, white light is preferably used as the detecting light.

Further, the light receiving unit 205 may include a plurality of CCD cameras arranged in a strip or a strip-like photodetector, and the detecting surfaces of the plurality of CCD cameras or the detecting surface of the strip-like photodetector serve(s) as the light receiving surface of the light receiving unit 205.

The plurality of CCD cameras can directly capture an image of the foreign object 106 on the surface of the substrate 10, or, brightness data of the reflected light can be acquired by the strip-like photodetector and then be processed, so as to obtain the position information of the foreign object 106 on the surface of the substrate 101.

Figure 8:
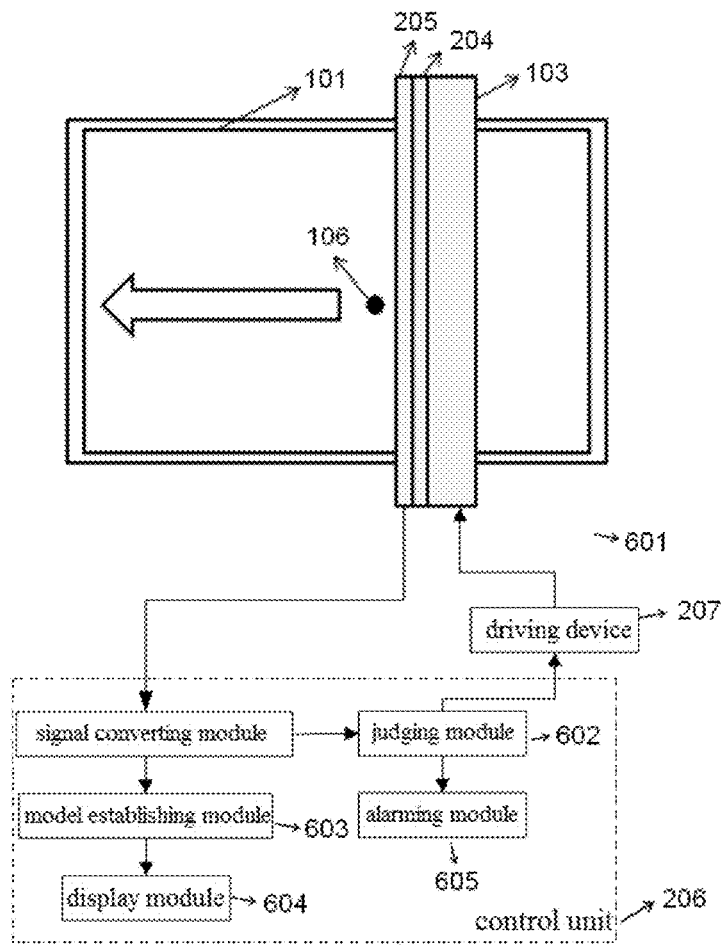
FIG. 8 is a schematic diagram of a coating system in an embodiment of the present disclosure.

The present disclosure further provides a coating system, and as shown in FIG. 8, the coating system includes a nozzle 103 and the above foreign object detecting device provided by the present disclosure. The foreign object detecting device includes a light emitting unit 204 and a light receiving unit 205, and is fixed in front of the nozzle 103 in the coating direction which is indicated by the hollow arrow in the figure. The light emitting unit 204 is arranged next to the nozzle 103, and the light receiving unit 205 is arranged in front of the light emitting unit 204 in the coating direction. During the coating process, firstly, the foreign object detecting device performs foreign object detection on the substrate 101 to be coated, and coating is then performed if no foreign object is detected, and in this way, it is conducive to discovering the foreign object promptly, and avoiding bad coating and a waste of material.

The coating system further includes a control unit 206, which is connected to the light receiving unit 205 to receive the optical signal from the light receiving unit 205, and is also connected to the nozzle 103 to transmit a control signal and the like to the nozzle 103. The control unit 206 can process the received optical signal and make a judgement, and if the control unit 206 judges that the brightness value of the reflected light from a certain reflective spot is smaller than a preset value according to the optical signal, it indicates that a foreign object is present at the reflective spot, and the coating system is thus controlled to stop operation.

As described above, the optical signal includes brightness distribution information of reflected light and position information of a reflective spot. When the foreign object 106 is present on or under the substrate 101, the brightness of the reflected light from the position corresponding to the foreign object 106 is lower than that of the reflected light from other position on the substrate 101, and the control unit 206 determines the position of the foreign object 106 based on the position where the reflected light has a reduced brightness, and controls the nozzle 103 to stop moving and coating upon discovery of a foreign object 106.

In the present disclosure, not only the foreign object 106 on the substrate 101 but also the foreign object 106 under the substrate 101 can be detected effectively, and the substrate 101 elevated by the foreign object 106 thereunder is prevented from colliding with the nozzle. In addition, in the present disclosure, the foreign object 106 can be detected in plan manner, which facilitates determining the specific position of the foreign object 106 more quickly. When the foreign object 106 is discovered, the control unit 206 can control the nozzle 103 to stop moving and coating promptly, so as to avoid bad coating.

Further, the coating system may further include a driving device 207, an output terminal of the driving device 207 is connected to the nozzle 103 to drive the nozzle 103 to move above the substrate 101, and a control terminal of the driving device 207 is connected to the control unit 206 to receive the control signal from the control unit 206. If the control unit 206 judges that the brightness value of the reflected light from a certain reflective spot is lower than the preset value according to the optical signal, the control unit 206 transmits a control signal to the control terminal of the driving device 207 to control the driving device 207 to stop outputting power to the nozzle 103.

The specific form of the driving device 207 is not limited in the present disclosure, for example, the driving device may be a motor, which can drive the nozzle 103 to move in the coating direction above the substrate 101.

Specifically, the control unit 206 may include a signal converting module 601 and a judging module 602.

The signal converting module 601 is used for converting the optical signal into an electrical signal which includes information on dimension of the foreign object and position of the foreign object. The term "dimension of the foreign object" herein includes an area occupied by the foreign object and a height of the foreign object. Generally, the larger size of the foreign object 106, the smaller brightness of the reflected light, so the specific position and dimension information of the foreign object 106 can be calculated according to the brightness distribution of reflected light.

The judging module 602 is used for comparing the dimension of the foreign object indicated by the electrical signal with a preset threshold dimension, to judge whether the dimension of the detected foreign object 106 exceeds a preset range or not.

In the present disclosure, the threshold dimension may be directly stored in the judging module 602, or provided in another storage module which can be accessed by the judging module 602, which is not limited herein.

Figure 9:
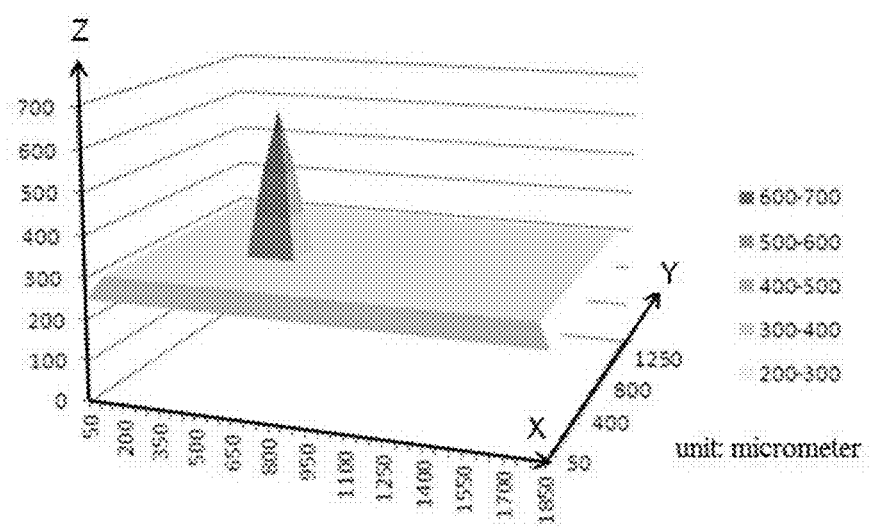
FIG. 9 is a schematic diagram of a three-dimensional model established by a model establishing unit included in a coating system in an embodiment of the present disclosure.

Further, in order that an operator can know the position and the dimension of the foreign object more intuitively, the control unit 206 may further include a model establishing module 603 and a display module 604. The model establishing module 603 is connected to the signal converting module 601 and is used for establishing a three-dimensional model according to the electrical signal obtained by the signal converting module 601. The three dimensional model presents state of the foreign object on the substrate, which includes the position of the foreign object on the substrate, the dimension of the foreign object (including the area occupied by the foreign object and the height of the foreign object) and the like, as shown in FIG. 9. The display module 604 is used for demonstrating the three-dimensional model.

Further, the control unit 206 may further include an alarming module 605 connected to the judging module 602. If the judging module 602 judges that the dimension of the foreign object exceeds the threshold dimension according to the electrical signal, the judging module 602 sends an abnormality signal to the alarm module 605, and the alarm module 605 sends out an alarming signal upon receipt of the abnormality signal to warn the operator to handle the abnormality.

To sum up, the coating system provided by the present disclosure can perform foreign object detection on a substrate to be coated in plan manner, and thus improves the efficiency of foreign object detection. In the meanwhile, in the present disclosure, not only a foreign object on the substrate but also a foreign object under the substrate can be detected effectively, which reduces the risk of bad coating, and in the meanwhile, the substrate elevated by a foreign object thereunder is prevented from colliding with the nozzle. In addition, the present disclosure can establish a three-dimensional model with respect to the dimension and the position of the foreign object, which facilitates detecting the foreign object more quickly and intuitively and improves yield of coating.

It can be understood that, the above implementations are merely exemplary implementations used for explaining the principle of the present disclosure, but the present disclosure is not limited thereto. For those skilled in the art, various modifications and improvements may be made without departing from the spirit and essence of the present disclosure, and these modifications and improvements are also deemed as falling within the protection scope of the present disclosure.

The invention claimed is:

1. A foreign object detecting device, comprising:
a light emitting unit and a light receiving unit arranged side by side, wherein, the light emitting unit is configured to emit light towards a surface of a substrate to be detected, and the light receiving unit is configured to detect an optical signal of reflected light reflected from the surface of the substrate to be detected and output the optical signal detected, and the optical signal includes brightness distribution information of the reflected light and position information of a reflective spot,
wherein the light emitting unit comprises a light transmissive box, a strip-shaped light source, a focusing lens disposed in the light transmissive box, and a slit arranged at one side of the light transmissive box facing the substrate to be detected, wherein an extending direction of the slit is the same as an extending direction of the strip-shaped light source, and light emitted from the strip-shaped light source exits via the slit after being converged by the focusing lens.

2. The foreign object detecting device according to claim 1, wherein, both the light emitting unit and the light receiving unit are strip-shaped, and lengths of both the light emitting unit and the light receiving unit are greater than or equal to width of the substrate to be detected.

3. The foreign object detecting device according to claim 1, wherein, the light emitting unit is configured to emit light perpendicular to the substrate to be detected.

4. The foreign object detecting device according to claim 1, wherein, the light emitting unit further comprises a light guide plate disposed between the strip-shaped light source and the focusing lens.

5. The foreign object detecting device according to claim 1, wherein, the strip-shaped light source comprises a strip-shaped light emitting diode, a plurality of light emitting diodes arranged in a strip-shaped dot matrix, or a strip-shaped laser transmitter.

6. The foreign object detecting device according to claim 1, wherein, the light receiving unit comprises a plurality of charge-coupled device (CCD) cameras arranged in a strip or a strip-shaped photodetector.

7. The foreign object detecting device according to claim 2, wherein, the light receiving unit comprises a plurality of charge-coupled device (CCD) cameras arranged in a strip or a strip-shaped photodetector.

8. The foreign object detecting device according to claim 3, wherein, the light receiving unit comprises a plurality of charge-coupled device (CCD) cameras arranged in a strip or a strip-shaped photodetector.

9. A coating system, comprising:
a nozzle and a foreign object detecting device, the foreign object detecting device comprising:
  a light emitting unit and a light receiving unit arranged side by side, wherein, the light emitting unit is configured to emit light towards a surface of a substrate to be detected, and the light receiving unit is configured to detect an optical signal of reflected light reflected from the surface of the substrate to be detected and output the optical signal detected, and the optical signal includes brightness distribution information of the reflected light and position information of a reflective spot,
  wherein the light emitting unit comprises a light transmissive box, a strip-shaped light source, a focusing lens disposed in the light transmissive box, and a slit arranged at one side of the light transmissive box facing the substrate to be detected, wherein an extending direction of the slit is the same as an extending direction of the strip-shaped light source, and light emitted from the strip-shaped light source exits via the slit after being converged by the focusing lens;
  wherein the foreign object detecting device is fixed in front of the nozzle in a coating direction.

10. The coating system according to claim 9, further comprising a control unit, which is connected to the light receiving unit of the foreign object detecting device to receive the optical signal from the light receiving unit, and is also connected to the nozzle to transmit a control signal to the nozzle, wherein the control unit is configured to process the optical signal received and make a judgement, and if the control unit judges that a brightness value of reflected light from a certain reflective spot is smaller than a preset value according to the optical signal, the coating system is controlled to stop operation.

11. The coating system according to claim 10, further comprising a driving device, wherein an output terminal of the driving device is connected to the nozzle to drive the nozzle to move above the substrate, and a control terminal of the driving device is connected to the control unit to receive the control signal from the control unit; if the control unit judges that the brightness value of reflected light from a certain reflective spot is smaller than the preset value according to the optical signal, the control unit transmits the control signal to the control terminal of the driving device, to control the driving device to stop outputting power to the nozzle.

12. The coating system according to claim 10, wherein, the control unit comprises a signal converting module and a judging module,
  the signal converting module is configured to convert the optical signal into an electrical signal which includes information on a dimension of a foreign object and a position of the foreign object, and
  the judging module is configured to compare the dimension of the foreign object indicated by the electrical signal with a preset threshold dimension, to judge whether the dimension of the foreign object detected exceeds a preset range or not.

13. The coating system according to claim 12, wherein, the control unit further comprises a model establishing module and a display module, the model establishing module is connected to the signal converting module, and is configured to establish a three-dimensional model, which presents a state of the foreign object on the substrate, according to the electrical signal obtained by the signal converting module, and the display module is configured to demonstrate the three-dimensional model.

14. The coating system according to claim 13, wherein, the state of the foreign object on the substrate includes the position of the foreign object on the substrate and the dimension of the foreign object.

15. The coating system according to claim 14, wherein, the dimension of the foreign object includes an area occupied by the foreign object and a height of the foreign object.

16. The coating system according to claim 12, wherein, the control unit further comprises an alarming module connected to the judging module; if the judging module judges that the dimension of the foreign object exceeds the preset threshold dimension according to the electrical signal, the judging module sends an abnormality signal to the alarming module, and the alarming module sends out an alarming signal upon receipt of the abnormality signal.

* * * * *